(12) United States Patent
Moriguchi et al.

(10) Patent No.: US 6,350,917 B1
(45) Date of Patent: Feb. 26, 2002

(54) α-CRYSTAL OF CYCLOPENTENONE (75) Inventors: Makoto Moriguchi; Katsushige Ikai; Masao Funakoshi; Hiroshi Kobori; Kazuyori Ochiai; Ikunoshin Kato, all of Otsu (JP)

(73) Assignee: Takara Shuzo Co., Ltd., Koyto (JP)

( * ) Notice: Subject to any disclaimer, the term of this patent is extended or adjusted under 35 U.S.C. 154(b) by 0 days.

(21) Appl. No.: 09/462,038

(22) PCT Filed: Aug. 19, 1998

(86) PCT No.: PCT/JP98/03696

§ 371 Date: Dec. 29, 1999

§ 102(e) Date: Dec. 29, 1999

(87) PCT Pub. No.: WO99/11595

PCT Pub. Date: Mar. 11, 1999

(30) Foreign Application Priority Data

Aug. 29, 1997 (JP) ............................................. 9-247577

(51) Int. Cl.[7] ............................................. C07C 49/597

(52) U.S. Cl. ........................ 568/379; 568/338; 568/343; 568/347; 568/361

(58) Field of Search ................................. 568/379, 338, 568/343, 347, 361

(56) References Cited

U.S. PATENT DOCUMENTS 6,087,401 A    7/2000    Koyama et al. ............ 514/690

OTHER PUBLICATIONS

Recherches dans la serie des cyclitols XLIV, Syntheses de cycloses derives du cyclopentrane; Helvectica Chimica Acta 1972, vol. 55 pp. 2838–2844 (Translation of summary only).
On the formation of reductic acid from pentoses or hexuronic acids; Carbohydrate Research 1993, vol. 274, pp. 217–222.

*Primary Examiner*—Sreeni Padmanabhan
(74) *Attorney, Agent, or Firm*—MacCord Mason PLLC (57) ABSTRACT

Crystals of trans-4,5-dihydroxy-2-cyclopenten-1-one of an α-type.

8 Claims, 5 Drawing Sheets

# α-CRYSTAL OF CYCLOPENTENONE

This application is a 371 of PCT/J898/03696 filed Aug. 19, 1998.

TECHNICAL FIELD OF THE INVENTION

The present invention relates to crystals of trans-4,5-dihydroxy-2-cyclopenten-1-one of an α-type having a physiological activity such as anticancer action useful in the fields of pharmaceuticals, foods and beverages.

PRIOR ART trans-4,5-dihydroxy-2-cyclopenten-1-one has a physiological activity such as anticancer action and is a compound useful in the fields of pharmaceuticals, foods and beverages.

With regard to a method for the manufacture of trans-4,5-dihydroxy-2-cyclopenten-1-one, a chemical synthesis [Carbohydrate Research, pages 217–222 (1993)] has been known. In addition, with regard to a practical manufacturing method, a method where uronic acid or uronic acid derivative (s) is/are heated and trans-4, 5-dihydroxy-2-cyclopenten-1-one is collected from the heated products is mentioned in WO98/13328. There is no description on crystals in trans-4,5-dihydroxy-2-cyclopenten-1-one obtained in the above-mentioned methods. With regard to a method for the manufacture of cis-4,5-dihydroxy-2-cyclopenten-1-one, there is a description in *Helvetica Chimica Acta,* volume 55, pages 2838–2844 (1972) and said compound was finally obtained as a sublimed substance.

Problems to be Solved by the Invention

Residue after concentration in vacuo and freeze-dried product of the aqueous solution of trans-4,5-dihydroxy-2-cyclopenten-1-one obtained by the above practical method are reddish brown syrupy substances usually containing 10–20% of water and they are difficult to handle and have no good thermostability.

An object of the present invention is to improve purity, thermostability and handling of trans-4,5-dihydroxy-2-cyclopenten-1-one.

Means to Solve the Problems

The present inventors have found that stable crystals having a specific X-ray diffraction pattern can be prepared when trans-4,5-dihydroxy-2-cyclopenten-1-one (hereinafter, just referred to as "the cyclopenten one") is extracted from an aqueous solution of the cyclopenten one with an organic solvent and the extract concentrated in vacuo is crystallized, when the cyclopentenone is extracted from a residue after concentration in vacuo or a freeze-dried substance of an aqueous solution of the cyclopentenone with an organic solvent and crystallization is conducted for the extract, or when a residue after concentration in vacuo or a freeze-dried substance of an aqueous solution of the cyclopentenone is dissolved in alcohol and then an organic solvent is added to said alcoholic solution whereupon the present inventors have named said crystals as "the cyclopentenone crystals of an α-type".

As compared with the conventional residue after concentration in vacuo or a freeze-dried substance of an aqueous solution of the cyclopentenone, this crystals of an α-type have been found to have significantly improved purity and much improved thermostability whereupon the present invention has been accomplished.

To sum up, the present invention relates to crystals of trans-4, 5-dihydroxy-2-cyclopenten-1-one of an α-type.

EMBODIMENTS OF THE INVENTION

The present invention will now be specifically illustrated as hereinafter.

The cyclopentenone used in the present invention may be synthesized by the above chemical synthetic method mentioned in Carbohydrate Research. Incidentally, the cyclopentenone is a compound which is produced in a product obtained by heating at least one substance selected from uronic acid, uronic acid derivative(s), saccharide compound containing uronic acid, saccharide compound containing uronic acid derivative(s), a substance which contains saccharide compound containing uronic acid, and a substance which contains saccharide compound containing uronic acid derivative(s) and, in the present invention, purified product thereof may be used.

Uronic acid is sometimes called glycuronic acid and is a general name for hydroxyaldehyde carboxylic acids in which an aldehyde group on aldose remains as it is while only a primary alcohol group at another end is oxidized to a carboxyl group. It is present in nature as a constituting ingredient for various polysaccharides of animals and plants. Examples of the polysaccharide containing uronic acid are pectin, pectic acid, alginic acid, hyaluronic acid, heparin, heparan sulfate, fucoidan, chondroitin sulfate, chondroitin, dermatan sulfate, etc. and they have been known to exhibit various physiological functions.

There is no particular limitation for the uronic acid used in the present invention. Thus, examples of the uronic acid are galacturonic acid, glucuronic acid, guluronic acid, mannuronic acid and iduronic acid while examples of the uronic acid derivative(s) are lactones, esters, amides, salts, etc. of the above-mentioned ones and any substance which produces the cyclopentenone on heating is covered by the derivative (s) of the present invention. Examples of the uronic acid lactone are glucurono-6,3-lactone (hereinafter, abbreviated as glucuronolactone), mannurono-6,3-lactone and idurono-6,3-lactone. Examples of the uronic acid ester are methyl, ethyl, propylene glycol and carboxymethyl uronates which can be manufactured from uronic acid. Uronic acid amide can be manufactured by amidation of uronic acid. Salts of them can be manufactured by common methods.

In this specification, the saccharide compound containing uronic acid or uronic acid derivative(s) means the saccharide compound containing uronic acid and/or uronic acid derivative(s). There is no particular limitation for the saccharide compound containing uronic acid and/or uronic acid derivative(s) and the examples applicable are pectin, pectic acid, alginic acid, hyaluronic acid, heparin, heparan sulfate, fucoidan, chondroitin sulfate, chondroitin and dermatan sulfate including decomposed products, derivative(s) of the decomposed products and salts of the decomposed products thereof which are chemically, enzymatically or physically-treated products thereof.

In the present invention, a substance which contains saccharide compound containing uronic acid and/or a substance which contains saccharide compound containing uronic acid derivative (s) mean(s) a substance containing a saccharide compound where uronic acid is contained and/or a substance containing a saccharide compound where uronic acid derivative (s) is contained and there is no particular limitation therefor so far as said substance contains the above-mentioned saccharide compound containing uronic acid and/or saccharide compound containing uronic acid derivative(s)

For example, when D-glucuronic acid is used a s a uronic acid and its 1% solution is heated at 121° C. for four hours, the cyclopentenone is produced in the heat-treated substance. The cyclopentenone in this heated substance is extracted with a solvent and the extract is concentrated. Then, this concentrated extract is separated by means of a silica gel column chromatography, the eluted cyclopentenone fraction is concentrated, the cyclopentenone is extracted with chloroform from the concentrate and the extract of the concentrate is subjected to a normal phase column chromatography whereupon the cyclopentenone in the heat-treated substance is purified.

Physical property of the cyclopentenone will be given as hereunder. Incidentally, a mass spectrometric analysis of the cyclopentenone was conducted using a mass spectrometer DX302 (manufactured by Nippon Denshi) Further, measurement of an NMR using heavy chloroform as a solvent was conducted by JNM-A 500 (manufactured by Nippon Denshi). Specific rotation was measured by a DIP-370 polarimeter (manufactured by Nippon Bunko) ; ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu).

FAB-MS m/z 115 [M+H]$^+$

Glycerol was used as a matrix.

$^1$H-NMR (CDCl$_3$)

δ4.20 (1H, d, J=2.4 Hz, 5-H), 4.83 (1H, m, 4-H), 6.30 (1H, dd, J=1.2, 6.1 Hz, 2-H), 7.48 (1H, dd, J=2.1, 6.1 Hz, 3-H)

Incidentally, the chemical shift value of the $^1$H-NMR was given on a basis that the chemical shift value of CHCl$_3$ was 7.26 ppm.

Those values nearly coincided with the data for cyclopentenone described in Carbohydrate Research.

Optical rotation: $[\alpha]_D^{20}$0° (c 1.3, water)

IR (KBr method): absorptions were noted at 3400, 1715, 1630, 1115, 1060, 1025 cm$^{-1}$.

UV: $\lambda_{max}$215 nm (water)

The cyclopentenone of an α-type according to the present invention may be manufactured by the following method for example.

There is no particular limitation for the method for the manufacture of the cyclopentenone and, for example, it may be manufactured by a method of Referential Examples 1 and 2 which will be mentioned later.

Examples of the organic solvent used in the present invention are ethyl acetate, butyl acetate, chloroform, ethyl ether, n-hexane, acetone, methanol, ethanol and acetic acid and said organic solvent may be used either solely or jointly as a mixture thereof. In the case of a sole solvent, ethyl acetate, butyl acetate, chloroform, ethyl ether, etc. may be used and, ethyl acetate and butyl acetate are particularly appropriate. In the case of a mixed solvent, crystallization takes place when ethyl acetate, butyl acetate, chloroform, ethyl ether or n-hexane is added to a solution of the cyclopentenone in methanol, ethanol or acetone and it is particularly suitable to add ethyl acetate and n-hexane to an ethanolic solution of the cyclopentenone to crystallize.

When crystallization of the cyclopentenone is conducted by a single organic solvent, it is preferred in view of purity and yield that a residue after concentration in vacuo or a freeze-dried substance is extracted, for example, with ethyl acetate and said extract is concentrated to give crystals.

For example, the residue after concentration in vacuo or the freeze-dried substance obtained in Referential Example 1 is extracted with ethyl acetate and the extract is concentrated and allowed to stand to give the crystals of an α-type.

In case a mixed solvent is used, the residue after concentration in vacuo or the freeze-dried substance is dissolved in a small amount of methanol or ethanol and then ethyl acetate and n-hexane are added thereto to give crystals.

For example, the residue after concentration in vacuo or the freeze-dried substance of the cyclopentenone obtained in Referential Example 1 is dissolved in a small amount of methanol or ethanol and then ethyl acetate and n-hexane are added thereto to give the crystals of an α-type. Amount of ethyl acetate and n-hexane to be added may vary depending upon the amount of methanol or ethanol used for dissolution and, in the case of an ethanolic solution, it is preferred to use ethyl acetate and n-hexane in the amounts of four-fold and two-fold, respectively.

Alternatively, butyl acetate and acetic acid are added to and mixed with an aqueous solution of the cyclopentenone so that the cyclopentenone is transferred to the resulting upper layer solution and is crystallized from the concentrated solution of said upper layer in vacuo. Incidentally, extraction of the cyclopentenone may be conducted, for example, under the condition of (an aqueous solution of the cyclopentenone):(butyl acetate):(acetic acid)= 1:1~50:0.1~10 or, preferably, (an aqueous solution of the cyclopentenone):(butyl acetate):(acetic acid)=1:2120:0.54 and the ratio of (an aqueous solution of the cyclopentenone) :(butyl acetate):(acetic acid) may be in such a manner that the cyclopentenone can be efficiently extracted and, in addition, the α-type crystals of the present invention can be efficiently obtained.

With regard to the concentration of the cyclopentenone, any concentration may be acceptable so far as crystallization takes place but, preferably, it is 10–1,000 mg/ml.

The temperature for allowing to stand is not limited to any particular temperature, provided that the temperature does not cause the degradation of cyclopentenone but, practically, it is from −20° C. to ambient temperature. Time required for crystallization is from one night to three days and, usually, crystals are obtained within one night. When α-type crystals which are previously prepared are added, it is possible to accelerate the crystallization.

The separated crystals are filtered by means of suction or centrifugation followed by drying whereupon the α-type crystals can be obtained.

As hereunder, explanation will be made for crystals of the cyclopentenone in an α-type according to the present invention.

1. Elementary Analysis

Elementary analysis was conducted for α-type crystals of the cyclopentenone of the present invention obtained in Example 3 which will be mentioned later using Yanagimoto CHN Coder Type MT-3. The result is given in Table 1.

TABLE 1

| Elements | C | H |
|---|---|---|
| Calculated (%) for $C_5H_6O_3$ | 52.63 | 5.30 |
| Found (%) for $C_5H_6O_3$ | 52.39 | 5.23 |

2. X-Ray Diffraction Pattern

X-ray diffraction pattern was measured for α-type crystals of the cyclopentenone of the present invention obtained in Example 1 which will be mentioned later using an X-Ray Diffractometer (RU-200; manufactured by Rigaku Denkisha) equipped with a scintillation counter detector and a Cu radiating device using a graphite monochrometer. The result is shown in Table 2 and in FIG. 1.

Figure 1:
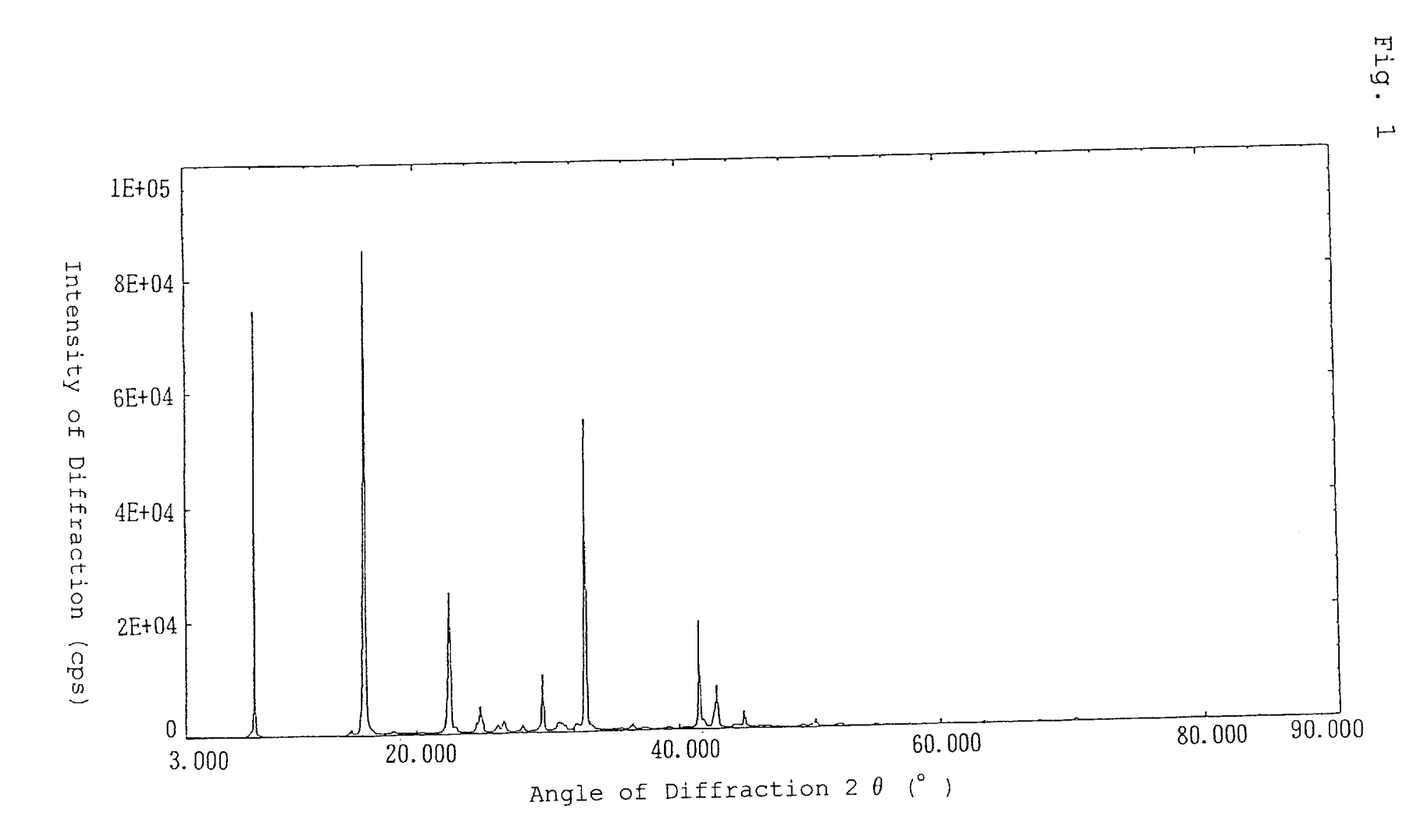
FIG. 1 is an X-ray diffraction pattern of α-type crystals of the cyclopentenone.

BRIEF DESCRIPTION OF THE DRAWINGS:

Thus, FIG. 1 is an X-ray diffraction pattern of α-type crystals of the cyclopentenone of the present invention showing in terms of the relation between angle of diffraction 2 θ(°, abscissa) and intensity of diffraction (cps, ordinate)

The expression "substantially having the following X-ray diffraction pattern" in the present invention means that the α-type crystals of the cyclopentenone of the present invention have the pattern of the following Table 2 as a characteristic pattern and that said pattern is within a range of variations which may be resulted due to a difference in the measuring instruments or in the conditions for preparing the sample.

TABLE 2

| d (Å) | $I/I_1$ | d (Å) | $I/I_1$ |
|---|---|---|---|
| 10.91 | 89 | 3.01 | 12 |
| 5.46 | 100 | 2.72 | 64 |
| 5.43 | 100 | 2.18 | 22 |
| 3.94 | 30 | 2.17 | 12 |
| 3.60 | 4 | 2.11 | 10 |
| 3.59 | 6 | 2.02 | 4 |

3. Thermal Analysis

Measurement was carried out by a Differential Scanning Calorimeter (DSC-50) of Shimadzu. Result of the differential scanning calorimetric analysis of the α-type crystals of the cyclopentenone of the present invention will be shown in FIG. 2.

Figure 2:
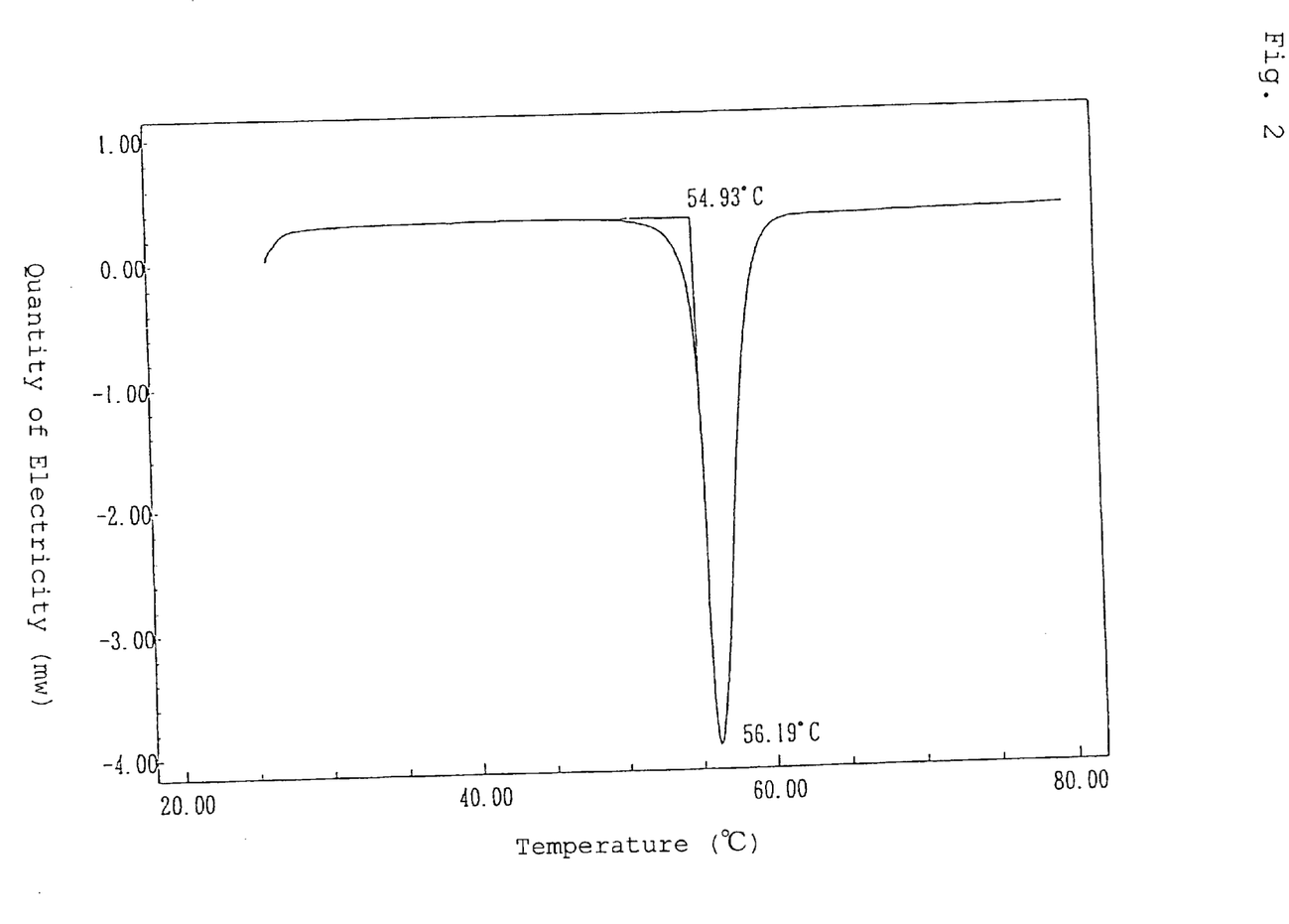
FIG. 2 shows the result of differential scanning calorimetric analysis of the α-type crystals.

Thus, FIG. 2 shows the result of differential scanning calorimetric analysis of the α-type crystals of the cyclopentenone of the present invention showing in terms of the relation between temperature (° C., abscissa) and quantity of electricity (mW, ordinate).

4. Purity

Figure 3:
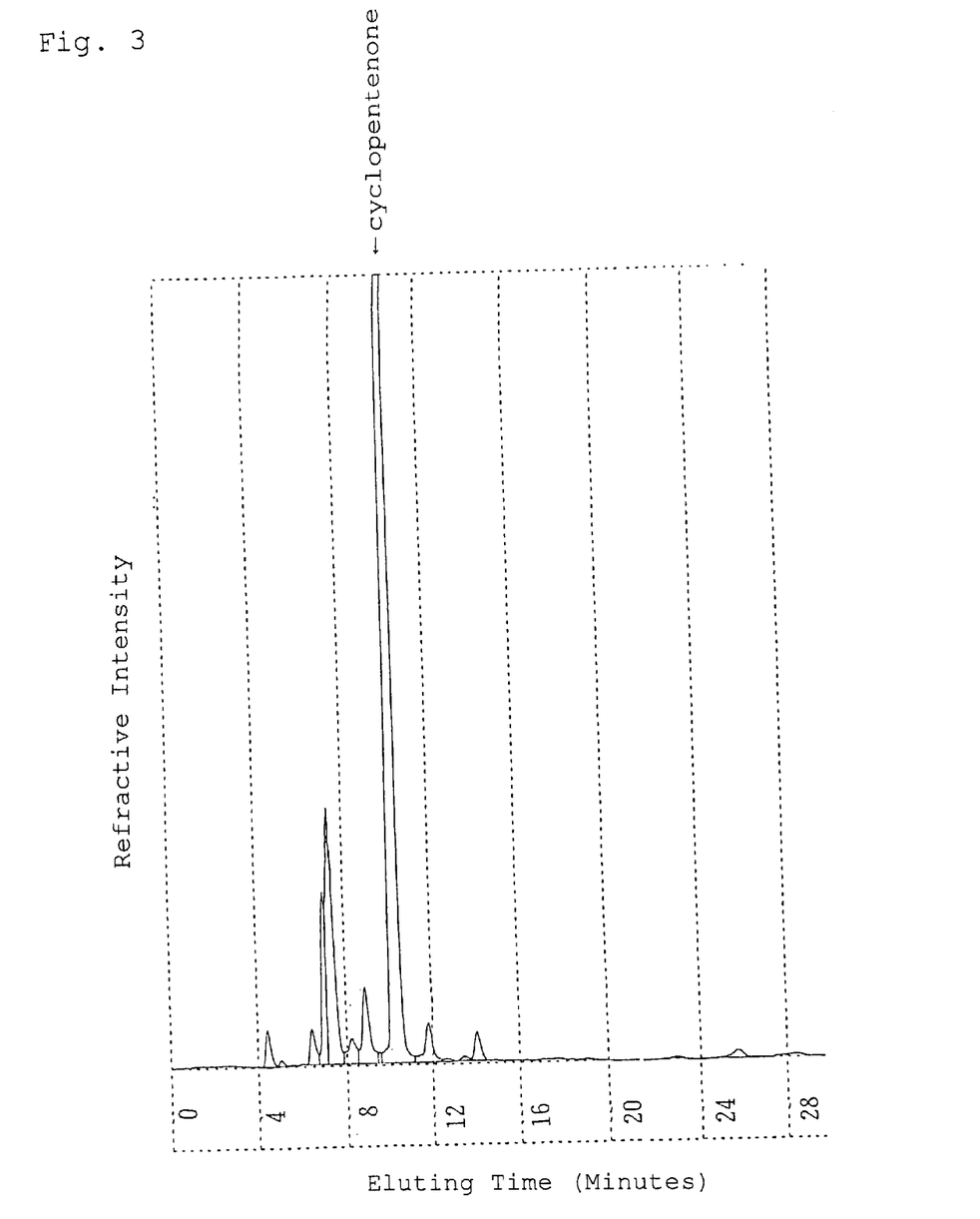
FIG. 3 shows the chromatogram of the freeze-dried product obtained in Referential Example 1.
Figure 4:
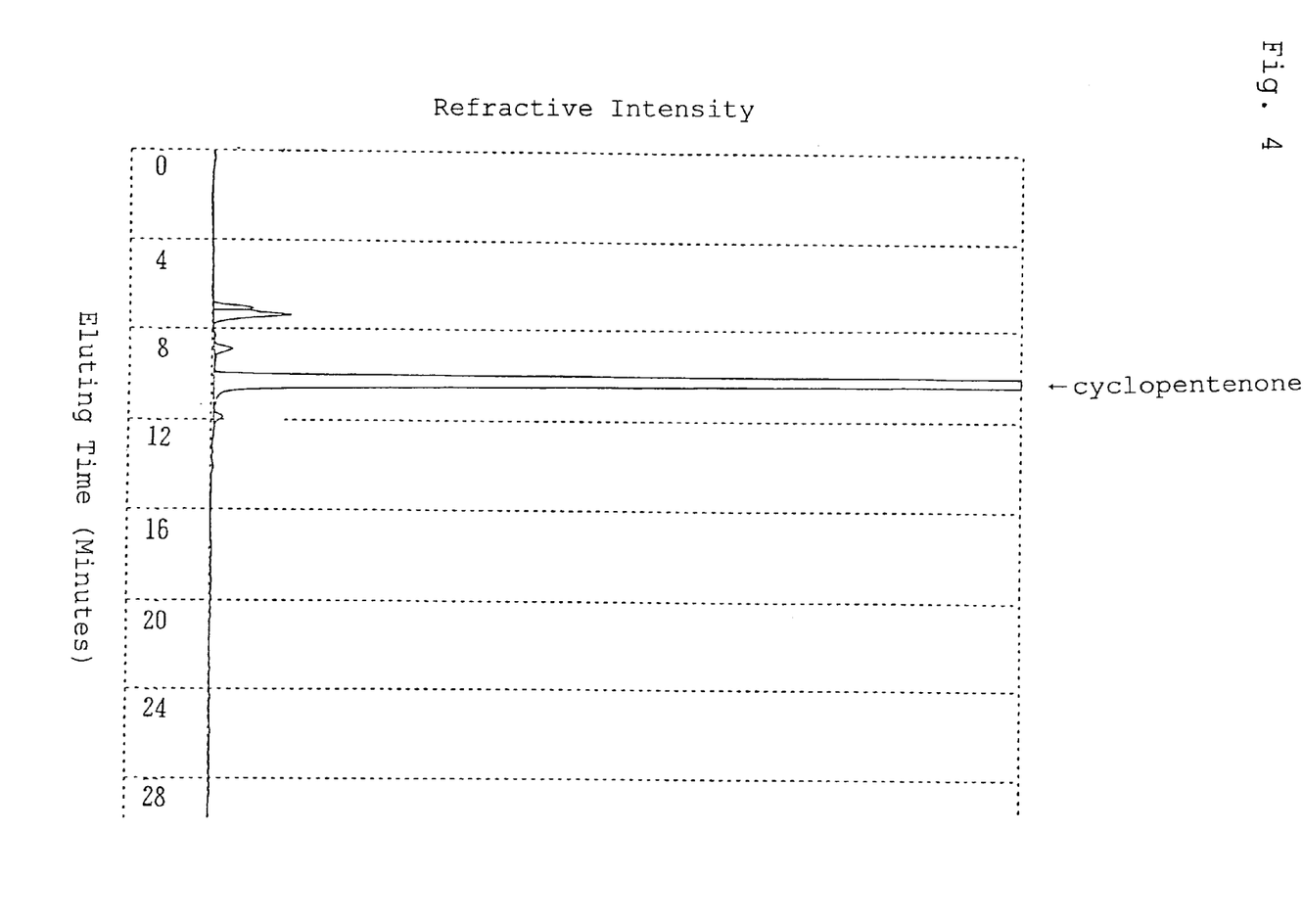
FIG. 4 shows the chromatogram of the α-type crystals obtained in Example 1.
Figure 5:
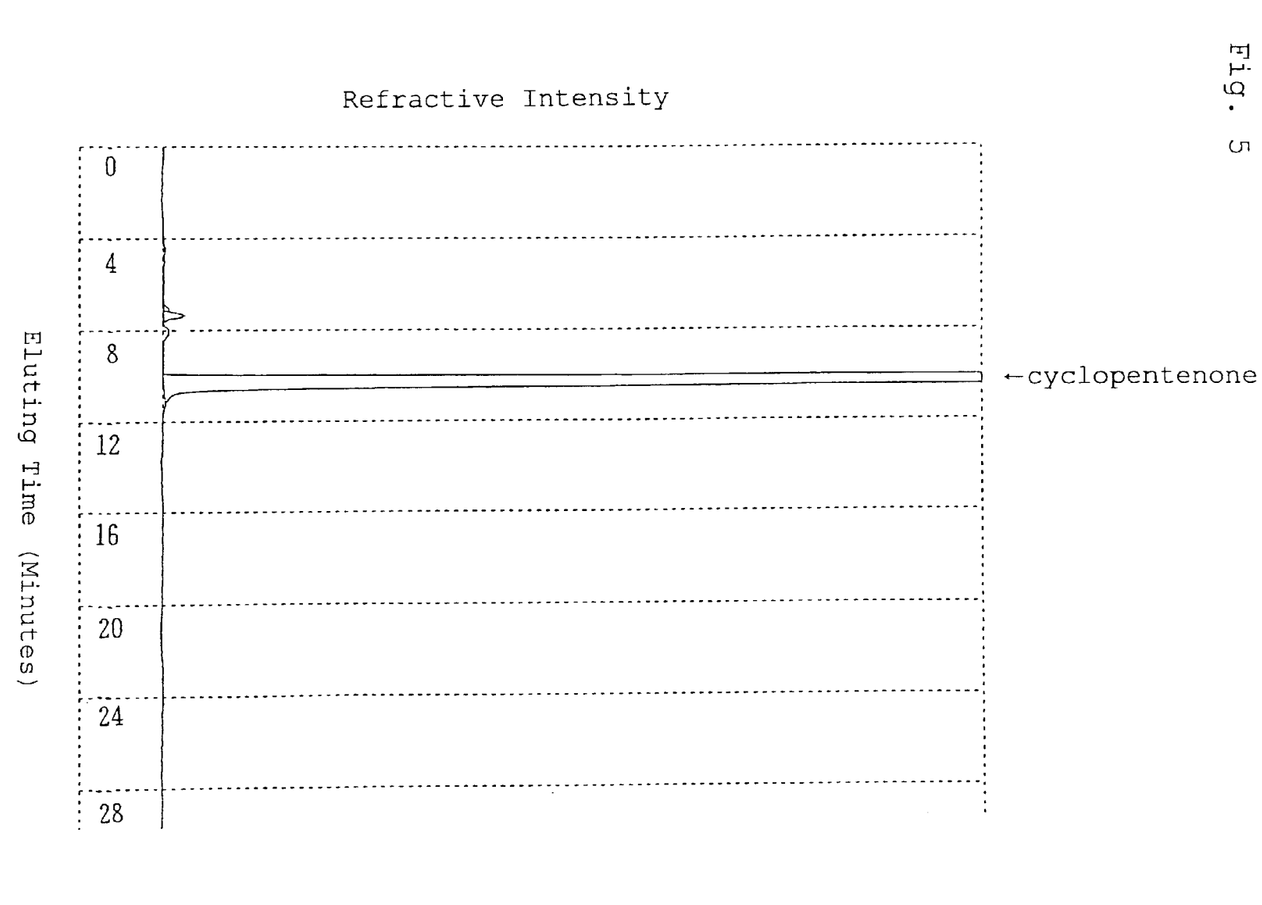
FIG. 5 shows the chromatogram of the α-type crystals obtained in Example 3.

A freeze-dried product of an aqueous solution of the cyclopentenone obtained in Referential Example 1 and the α-type crystals obtained in Examples 1 and 3 which will be mentioned later were analyzed by the following conditions using a High Performance Liquid Chromatographic Apparatus of Shimadzu and the purity obtained from the area percentage of the chromatograms is shown in Table 3. Chromatogram of the freeze-dried product is shown in FIG. 3. Chromatogram of the α-type crystals obtained in Example 1 is shown in FIG. 4. Chromatogram of the α-type crystals obtained in Example 3 is shown in FIG. 5. In FIG. 3 to FIG. 5, the ordinate indicates refractive intensity while the abscissa indicates eluting time (minutes).

Conditions for Chromatography

Column: DAISOPAK SP-120-5-ODS-BP (manufactured by Daiso) 4.6 mm×25 cm

Column temperature: 40° C.

Mobile phase: a 0.01% aqueous solution of trifluoroacetic acid

Flow rate: 0.5 ml/minute

Detector: Differential refractometer

Amount of the sample injected: 1 µl (10 mg/ml)

TABLE 3

| | Freeze-Dried Product (Referential Example 1) | α-Type Crystals (Example 1) | α-Type Crystals (Example 3) |
|---|---|---|---|
| Purity (%) | 71.2 | 96.7 | 99.5 |

Incidentally, "purity (%)" is that the peak area of the cyclopentenone of chromatogram obtained by a high performance chromatography is divided by the sum of the total peak areas followed by multiplying by 100. Accordingly, it stands for the ratio of the amount of the cyclopentenone in a solid which contains no water.

As shown in Table 3, the α-type crystals of the cyclopentenone of the present invention shows a significantly improved purity than the freeze-dried product.

5. Thermostability

In order to compare the thermostability of the freeze-dried cyclopentenone obtained in Referential Example 1 and that of the α-type crystals obtained in Example 1, quantitative determination was conducted for the cyclopentenone on the initial stage and after allowing to stand at 40° C. for six days by means of the following quantitative determination method. The result is given in Table 4.

Quantitative Determination Method: A sample (0.1 g) of the cyclopentenone is dissolved in 100 ml of water and 2 ml of the resulting solution are diluted to an extent of 50-fold. Absorbance (A) of this solution at the wave length of maximum absorption near the wave length of 215 nm is measured. Amount of the cyclopentenone (mg/ml) is calculated by the following formula.

Amount of the Cyclopentenone (mg/ml)=$(A \div 773.4) \times 50000$

TABLE 4

| | Amount of the Cyclopentenone (%) | |
|---|---|---|
| | At Initial Stage | After Standing at 40° C. for six days |
| Freeze-Dried Product | 59.4 | 28.2 |
| α-Type Crystals | 96.4 | 95.2 |

The amount (%) in Table 4 shows the ratio (%) of the amount of the cyclopentenone in the sample where the substances which are other than the cyclopentenone are water and impurities.

As shown in Table 4, the α-type crystals of the cyclopentenone of the present invention showed significantly improved thermostability as compared with the freeze-dried product.

EXAMPLES

A method for the manufacture of the cyclopentenone crystals of an α-type in accordance with the present invention will now be further illustrated by way of the following examples although the present invention is not limited to those examples only.

Referential Example 1

Commercially available glucuronolactone (manufactured by Nacalai Tesque) (500 g) was dissolved in 38 liters of water and then steam was blown thereinto to heat at 125° C. for five hours. After cooling, this was concentrated in vacuo and the concentrate was adjusted to pH 5.0 by NaOH. This solution was charged to a column (20 liters) of an anionic exchanger using Diaion SA-10A (manufactured by Mitsubishi Chemical) which was previously equilibrated with water followed by eluting with water to give 24 liters of a non-adsorbing fraction.

This fraction was concentrated in vacuo to 2.8 liters, NaCl was added thereto to make its final concentration 2M, and the mixture was charged, by splitting into two, to a column (15 liters) of a synthetic adsorbent (SP-207; manufactured by Mitsubishi Chemical) which was previously equilibrated with a 2M aqueous solution of NaCl. The column was washed with a 2M aqueous solution of NaCl and a fraction (78 liters in total) which was eluted with a 0.1M aqueous solution of NaCl was obtained.

This fraction was concentrated in vacuo to 11 liters and the concentrate was subjected to the same SP-207 column chromatography as above to give 24 liters of an eluate. In this case, however, all sample was subjected to one chromatographic operation and elution was conducted with water.

The eluate was concentrated in vacuo to 100 ml and desalted by means of electrodialysis using a permeable membrane (AC-110-10; manufactured by Asahi Chemical Industry) to give 100 ml of a 6% solution of the cyclopentenone. This cyclopentenone solution was concentrated in vacuo to prepare a concentrated residue in reddish brown color. This cyclopentenone solution was freeze-dried to prepare a reddish brown freeze-dried product as well.

Referential Example 2

Glucuronolactone (500 g) was dissolved in 38 liters of water and then steam was blown thereinto to heat at 125° C. for five hours. After cooling, the solution was concentrated in vacuo and the concentrate was charged to a column (20 liters) of an anionic exchanger using Diaion SA-10A which was previously equilibrated with water to give 73 liters in total of the non-adsorbed fraction being eluted with water and the passing-through solution.

This fraction was concentrated in vacuo to 3 liters, NaCl was added thereto to make its final concentration 2M and was charged, by splitting into two, to a column (15 liters) of a synthetic adsorbent (SP-207) which was previously equilibrated with a 2M aqueous solution of NaCl. The column was washed with a 2M aqueous solution of NaCl and eluted with a 0.1M aqueous solution of NaCl to give 73 liters of a fraction in total.

This fraction was concentrated in vacuo to 3 liters and the concentrate was subjected to the same SP-207 column chromatography as above to give 30 liters of eluate. In this case, however, all sample was subjected to one chromatographic operation and elution was conducted with water.

The eluate was concentrated in vacuo to 150 ml and desalted by means of electrodialysis using a permeable membrane (AC-100-10; manufactured by Asahi Chemical Industry) to give 150 ml of a 7.2% solution of the cyclopentenone.

Example 1

Ethyl acetate (1.5 liters) was added to 120 g of the freeze-dried cyclopentenone obtained in Referential Example 1 and heated at 60° C. to extract. The resulting extract with ethyl acetate was dried over anhydrous magnesium sulfate and concentrated in vacuo. The concentrated residue was dissolved in 0.5 liter of ethyl acetate with heating and allowed to stand overnight at 5° C. to crystallize. The resulting crystals were sucked followed by drying in vacuo to give 50.9 g of crystals of an α-type in pale yellow color.

Example 2

The residue (10 g) of the cyclopentenone after concentrating in vacuo obtained in Referential Example 1 was dissolved in 5 ml of ethanol, then 20 ml of ethyl acetate and 10 ml of n-hexane were added thereto and a small amount of the α-type crystals obtained in Example 1 was added followed by allowing to stand overnight at 5° C. The crystals separated out therefrom were sucked and dried in vacuo to give 4.3 g of the α-type crystals in pale yellow color.

Example 3

Ethyl acetate (50 ml) was added to 10 g of the α-type crystals obtained in Example 1 and was heated to dissolve. After cooling, the α-type crystals obtained in Example 2 were added thereto followed by allowing to stand overnight at 10° C. to crystallize. The resulting crystals were sucked and dried in vacuo to give 7.6 g of the α-type crystals in pale yellow color.

Example 4

A mixture of 266 ml of butyl acetate and 206.6 ml of acetic acid was mixed with 26.6 ml of a 7.2% solution of the cyclopentenone mentioned in Referential Example 2 followed by stirring whereupon the cyclopentenone was extracted therefrom in the upper layer (the primary extract). A mixture of butyl acetate and acetic acid (5:1 by volume) was added to and mixed with 1 (by volume) of the lower layer followed by stirring and the resulting upper layer was recovered (the secondary extract). The primary and the secondary extracts were combined and concentrated in vacuo to give 15.5 ml of the concentrated extract. The α-type crystals obtained in Example 1 were added to said solution at 5° C. and, when a few crystals were separated out therefrom, the solution was allowed to stand overnight at −20° C. to crystallize. The resulting crystals were sucked and dried in vacuo to give 492 mg of the α-type crystals in pale yellow color.

Merit of the Invention

The cyclopentenone of an α-type crystals in accordance with the present invention is quite effective in obtaining the cyclopentenone of a high purity in large quantities and is easily operated in manufacturing the cyclopentenone preparations. In addition, it has a significantly improved color and thermostability as compared with the freeze-dried product.

What is claimed is:

1. Crystals of trans-4,5-dihydroxy-2-cyclopenten-1-one.
2. The crystals according to claim 1 wherein said crystals are α-type crystals.

3. The crystals according to claim 2 wherein said α-type crystals substantially have the following X-ray diffraction pattern:

| d(Å) | I/I$_1$ | d(Å) | I/I$_1$ |
|---|---|---|---|
| 10.91 | 89 | 3.01 | 12 |
| 5.46 | 100 | 2.72 | 64 |
| 5.43 | 100 | 2.18 | 22 |
| 3.94 | 30 | 2.17 | 12 |
| 3.60 | 4 | 2.11 | 10 |
| 3.59 | 6 | 2.02 | 4 |

4. A method for preparation of crystals of trans-4,5-dihydroxy-2-cyclopenten-1-one comprising crystallizing trans-4,5-dihydroxy-2-cyclopenten-1-one in a water-insoluble organic solvent.

5. The method according to claim 4 wherein said water-insoluble organic solvent is selected from the group consisting of: ethyl acetate, chloroform, ethyl ether, n-hexane and butyl acetate.

6. The method according to claim 5 wherein said water-insoluble organic solvent is selected from the group consisting of: ethyl acetate and butyl acetate.

7. The method according to claim 4 wherein said crystals are α-type crystals.

8. The method according to claim 7 wherein said crystals are α-type crystals substantially having the following X-ray diffraction pattern:

| d(Å) | I/I$_1$ | d(Å) | I/I$_1$ |
|---|---|---|---|
| 10.91 | 89 | 3.01 | 12 |
| 5.46 | 100 | 2.72 | 64 |
| 5.43 | 100 | 2.18 | 22 |
| 3.94 | 30 | 2.17 | 12 |
| 3.60 | 4 | 2.11 | 10 |
| 3.59 | 6 | 2.02 | 4 |

* * * * *